United States Patent
Fischer et al.

(10) Patent No.: US 7,223,820 B2
(45) Date of Patent: May 29, 2007

(54) AMINE HARDENER FOR EPOXY RESINS

(75) Inventors: Walter Fischer, Reinach (CH);
Claudio A Gabutti, Therwil (CH);
Isabelle Frischinger, Riespach (FR);
Rolf Wiesendanger, Riehen (CH)

(73) Assignee: Huntsman Advanced Materials Americas, Inc., The Woodlands, TX (US)

( * ) Notice: Subject to any disclaimer, the term of this patent is extended or adjusted under 35 U.S.C. 154(b) by 269 days.

(21) Appl. No.: 10/815,532

(22) Filed: Mar. 31, 2004

(65) Prior Publication Data

US 2004/0186268 A1    Sep. 23, 2004

Related U.S. Application Data

(62) Division of application No. 10/031,983, filed as application No. PCT/EP00/06931 on Jul. 20, 2000, now Pat. No. 6,759,506.

(51) Int. Cl.
*C08L 63/00* (2006.01)
*C08L 63/02* (2006.01)
*C08L 63/04* (2006.01)

(52) U.S. Cl. ............... 525/523; 525/418; 525/504; 525/524

(58) Field of Classification Search ............... None
See application file for complete search history.

(56) References Cited

U.S. PATENT DOCUMENTS

| | | | |
|---|---|---|---|
| 2,831,830 A | 4/1958 | Schroeder | |
| 3,394,098 A | 7/1968 | Cameron | |
| 3,548,002 A | 12/1970 | Levine | |
| 3,919,277 A | 11/1975 | Luhowy et al. | |
| 5,086,091 A | 2/1992 | Geist et al. | 523/415 |
| 5,143,999 A | 9/1992 | Setiabudi et al. | 528/109 |

FOREIGN PATENT DOCUMENTS

| | | |
|---|---|---|
| CH | 586732 | 4/1977 |
| DE | 1595395 | 4/1970 |
| EP | 0273170 B1 | 7/1988 |
| EP | 0449776 A2 | 10/1991 |
| JP | 51082400 | 7/1976 |
| JP | 07173283 | 7/1995 |
| JP | 07228567 | 8/1995 |

*Primary Examiner*—Robert Sellers

(57) ABSTRACT

Compounds of formula Ia or Ib

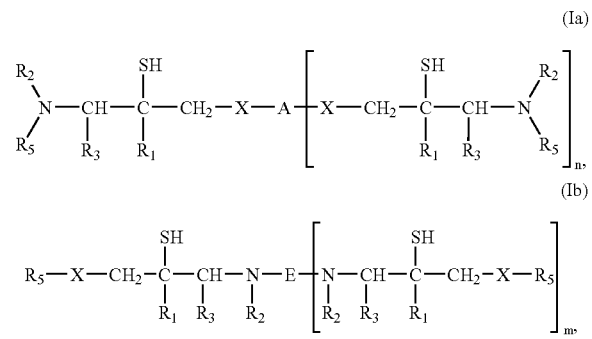

wherein A is an (n+1)-valent aliphatic, cycloaliphatic, araliphatic or aromatic radical and n is an integer from 0 to 5,
E is an (m+1)-valent aliphatic, cycloaliphatic, araliphatic or aromatic radical and m is an integer from 0 to 3,
X is —O—, —C(=O)O— or —CHR$_4$—, with R$_4$ and R$_3$ together forming an ethylene group,
R$_1$ and R$_2$ are, each independently of the other, hydrogen or methyl,
R$_3$ is hydrogen, or R$_3$ and R$_4$ together form an ethylene group,
and R$_5$ is a monovalent aliphatic, cycloaliphatic, araliphatic or aromatic radical,
are highly reactive curing agents for epoxy resins and yield cured products having improved resistance to chemicals.

15 Claims, No Drawings

AMINE HARDENER FOR EPOXY RESINS

This application is a divisional of application Ser. No. 10/031,983, filed Jan. 25, 2002 now U.S. Pat. No. 6,759,506, which is the National Stage of International Application No. PCT/EP00/06931, filed Jul. 20, 2000.

The present invention relates to polymercaptopolyamines, to a process for the preparation thereof, to epoxy resin compositions comprising such polymercaptopolyamines and to the use of those compositions.

U.S. Pat. No. 5,143,999 describes mixtures of polyamines and of dithiols derived from polyoxyalkylene glycols as hardeners for epoxy resins. The cured products produced therefrom are distinguished by a high degree of flexibility and good viscoelastic properties combined with good strength and hardness values.

The problem of the present invention was to provide curing agents for epoxy resins which yield cured products having improved resistance to chemicals.

It has now been found that certain polymercaptopolyamines are highly reactive with respect to epoxy resins even at low temperatures and that the cured products obtained therefrom have both improved resistance to chemicals and increased resistance to weathering.

The present invention relates to compounds of formula Ia or Ib,

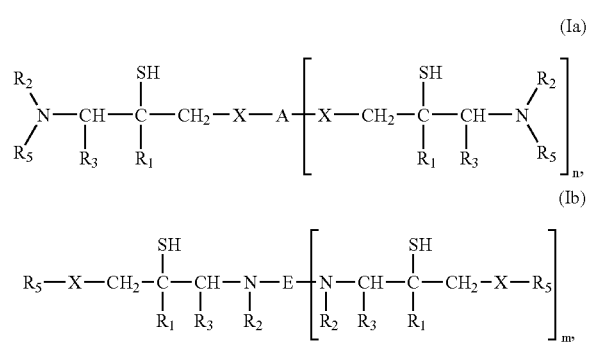

wherein A is an (n+1)-valent aliphatic, cycloaliphatic, araliphatic or aromatic radical and n is an integer from 0 to 5, E is an (m+1)-valent aliphatic, cycloaliphatic, araliphatic or aromatic radical and m is an integer from 0 to 3, X is —O—, —C(=O)O or —CHR$_4$—, with R$_4$ and R$_3$ together forming an ethylene group, R$_1$ and R$_2$ are, each independently of the other, hydrogen or methyl, R$_3$ is hydrogen, or R$_3$ and R$_4$ together form an ethylene group, and R$_5$ is a monovalent aliphatic, cycloaliphatic, araliphatic or aromatic radical.

In formula Ia, A can, in principle, be any mono- to hexa-valent epoxy radical. Preference is given to bi-, tri- and tetra-valent radicals.

Examples of aliphatic radicals are ethylene, propylene, tetramethylene, hexamethylene, poly(oxyethylene), poly(oxypropylene), poly(oxytetramethylene), 2-methyl-1,5-pentanediyl, 2,2,4-trimethyl-1,6-hexanediyl, 2,4,4-trimethyl-1,6-hexanediyl and the radicals of aliphatic alcohols after removal of the OH groups, for example the radicals of trimethylolpropane, pentaerythritol and dipentaerythritol.

Cycloaliphatic radicals are, for example, cyclopentyl, cyclohexyl, 1,3-cyclopentylene, 4-methyl-1,3-cyclopentylene, 1,2-cyclohexylene, 1,3-cyclohexylene, 1,4-cyclohexylene, 4-methyl-1,3-cyclohexylene, 2,5-norbornanediyl, 2,6-norbornanediyl, 7,7-dimethyl-2,5-norbornanediyl, 7,7-dimethyl-2,6-norbornanediyl, cyclohexane-1,3-dimethylene, cyclo-hexane-1,4-dimethylene, 3-methylene-3,5,5-trimethylcyclohexylene (isophorone), norbornane-2,5-dimethylene, norbornane-2,6-dimethylene, 7,7-dimethylnorbornane-2,5-dimethylene and 7,7-dimethylnorbornane-2,6-dimethylene and the radicals of cycloaliphatic alcohols after removal of the OH groups, for example the radicals of hydrogenated bisphenol A and hydrogenated bisphenol F.

Suitable araliphatic radicals are, for example, benzyl, the radicals of 1,2-, 1,3- and 1,4-bis(hydroxymethyl)benzene, the radicals of 1,2,3-, 1,2,4-, 1,2,5- and 1,3,5-tris(hydroxymethyl)benzene and the radicals of bis(hydroxymethyl)naphthalene. Examples of aromatic radicals are phenyl, naphthyl, the radicals of bisphenols, for example bisphenol A, bisphenol F and dihydroxybiphenyl, and the radicals of phenol novolaks and cresol novolaks.

Preference is given to compounds of formula Ia wherein X is —O— and A is a bivalent radical of a bisphenol or of a cycloaliphatic diol, the radical of a phenol novolak or cresol novolak, the bi- to tetra-valent radical of an isocyanate/polyol adduct or the tri- to hexa-valent radical of a tri- to hexa-functional aliphatic polyol.

Special preference is given to compounds of formula Ia wherein X is —O— and A is a bivalent radical of formula

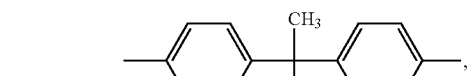

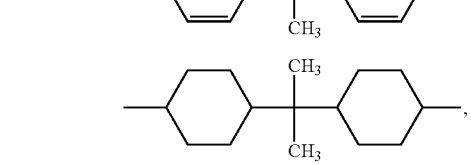

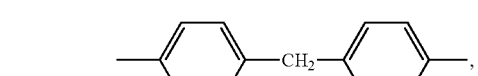

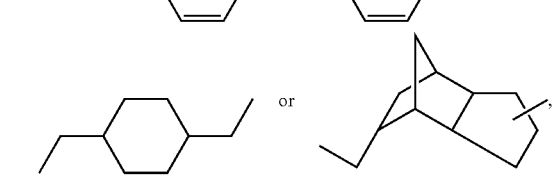

the radical of a phenol novolak or cresol novolak, a trivalent radical of formula

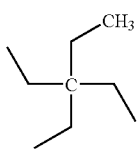

or

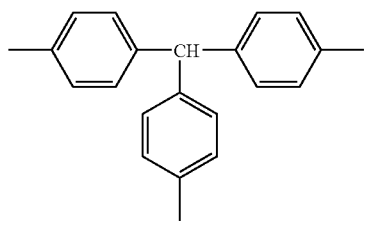

or the tetravalent radical of formula

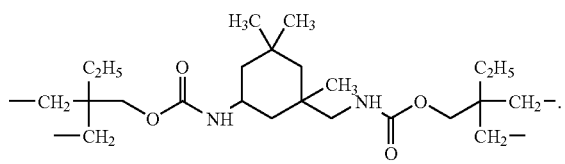

$R_5$ in formulae Ia and Ib is preferably $C_1$–$C_{20}$alkyl, $C_5$–$C_{12}$cycloalkyl, $C_6$–$C_{10}$aryl or $C_7$–$C_{12}$aralkyl, each of which is unsubstituted or substituted by one or more amino groups, hydroxyl groups, $C_1$–$C_8$alkoxy groups or halogen atoms.

Alkyl groups that are suitable as $R_5$ are, for example, methyl, ethyl, isopropyl, n-propyl, n-butyl, isobutyl, sec-butyl, tert-butyl and the various isomers of pentyl, hexyl, heptyl, octyl, nonyl, decyl, undecyl, dodecyl, tridecyl, tetradecyl, pentadecyl, hexadecyl, heptadecyl and octadecyl groups.

Cycloalkyl is preferably $C_5$–$C_8$cycloalkyl, especially $C_5$- or $C_6$-cycloalkyl. Examples include cyclopentyl, methylcyclopentyl, cyclohexyl, cycloheptyl and cyclooctyl.

Aralkyl contains preferably from 7 to 12 carbon atoms and especially from 7 to 10 carbon atoms and may be, for example, benzyl, phenethyl, 3-phenylpropyl, α-methylbenzyl, 4-phenylbutyl and α,α-dimethylbenzyl.

Aryl groups are, for example, phenyl, tolyl, mesityl, isityl, naphthyl and anthryl.

Preference is given to compounds of formulae Ia and Ib wherein $R_5$ is $C_2$–$C_{10}$alkyl, $C_2$–$C_{10}$aminoalkyl, phenyl, benzyl, cyclohexyl or a radical of formula $H_2N$—Z—$CH_2$—NH—, wherein Z is a bivalent cycloaliphatic, araliphatic or aromatic radical or a radical of formula —$(CH_2CH_2NH)_k$—$CH_2$—, wherein k is 2 or 3.

Suitable radicals Z are, for example, the bivalent radicals mentioned for A hereinbefore.

Special preference is given to compounds of formulae Ia and Ib wherein $R_5$ is n-butyl, n-octyl, cyclohexyl, benzyl, 2-aminoethyl, 4-(aminomethyl)pentyl, 5-amino-2-methylpentyl, 3-dimethylaminopropyl, 3-methylaminopropyl, 4-aminocyclohexyl or a radical of formula —$CH_2CH_2NHCH_2CH_2NH_2$,

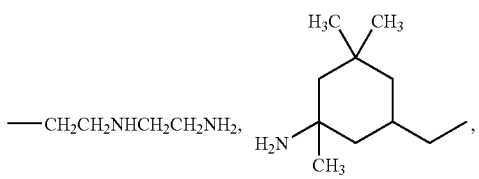

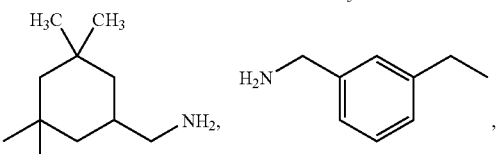

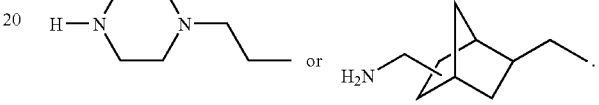

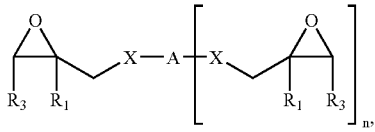

or

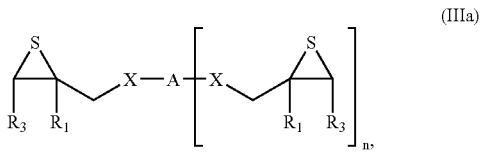

Preference is given also to compounds of formula Ia or Ib wherein X is O— and $R_1$ and $R_3$ are hydrogen.

The compounds of formula Ia can be prepared in accordance with known methods from the epoxy compounds of formula IIa:

$$\text{(IIa)}$$

wherein A, X, $R_1$, $R_3$ and n are as defined hereinbefore.

In such methods, the epoxy compound of formula IIa is, in a first reaction step, converted by reaction with thiourea or an alkali-metal or ammonium thiocyanate, preferably potassium thiocyanate, into the episulfide of formula IIIa $$\text{(IIIa)}$$

the thiourea or thiocyanate advantageously being used in an amount such that there are from 0.8 to 1.2 equivalents of sulfur for one epoxy equivalent.

The reaction can be carried out in aprotic or protic organic solvents or mixtures thereof. Preference is given to alcohols, for example methanol and ethanol, and aromatic hydrocarbons, for example toluene and xylene. The addition of co-solvents, for example ethers or carboxylic acids, can speed up the reaction.

The reaction can be carried out at room temperature and also at elevated temperature; the preferred reaction temperature is from 60 to 100° C.

The episulfide of formula IIIa can be isolated by separating off the by-products by means of filtration, extraction, phase separation and subsequent concentration by evaporating off the solvent.

It is also possible, however, for the episulfide of formula IIIa to be further processed directly, in the form of the crude product in solution, without separating off the by-products.

The episulfide of formula IIIa is then dissolved in an aprotic or protic organic solvent and, under inert gas (argon or nitrogen), reacted with the amine $R_5$—NH—$R_2$, the amount of the amine $R_5$—NH—$R_2$ preferably being so selected that there are from 1 to 10 amine groups for one episulfide group. Preferred solvents are alcohols (e.g. methanol, ethanol, tert-butanol) and aromatic hydrocarbons, for example toluene and xylene.

Preferably, the amine $R_1$—$NH_2$ is also used in the form of a solution in one of the above-mentioned organic solvents.

The reaction is advantageously carried out at elevated temperature, preferably at from 40° C. to 120° C.

The compounds of formula Ia according to the invention can be isolated by distilling off the solvent under reduced pressure. The excess amine $R_5$—NH—$R_2$ can then likewise be removed by distillation at elevated temperature. In a particular embodiment of the invention, the amine $R_5$—NH—$R_2$ is used as co-hardener, in which case separation of the product of formula Ia and the amine $R_5$—NH—$R_2$ is not necessary; rather, the reaction product can be used as a hardener for epoxy resins without further working-up. That procedure is recommended especially when using di- or poly-amines.

The present invention accordingly relates also to a process for the preparation of compounds of formula Ia by reacting a compound of formula IIa

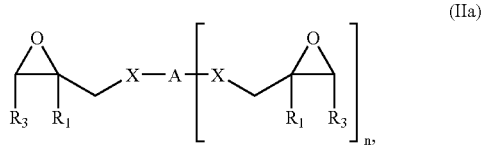

(IIa)

wherein A, X, $R_1$, $R_3$ and n are as defined hereinbefore, with thiourea or a thiocyanate and subsequently reacting the resulting episulfide with an amine of formula $R_5$—NH—$R_2$ wherein $R_5$ and $R_2$ are as defined hereinbefore.

The compounds of formula Ib can be prepared analogously from the corresponding epoxy compounds of formula IIb.

The invention accordingly relates further to a process for the preparation of compounds of formula Ib by reacting a compound of formula IIb

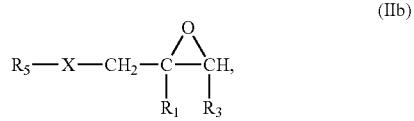

(IIb)

wherein X, $R_1$, $R_3$ and $R_5$ are as defined hereinbefore, with thiourea or a thiocyanate and subsequently reacting the resulting episulfide with a polyamine of formula E—$(NHR_2)_{m+1}$ wherein E, $R_2$ and m are as defined hereinbefore.

Episulfides can, for example, also be synthesized from the corresponding epoxides by reaction with triphenylphosphine sulfide.

In addition, episulfides can be prepared according to known-methods directly from the corresponding alkenes, for example by reaction with m-chloroperbenzoic acid and subsequent reaction with thiourea in the presence of $H_2SO_4$, by reaction with propylene sulfide in the presence of rhodium catalysts and also by reaction with (diethoxyphosphoryl)sulfenyl chloride, (diethoxythiophosphoryl)sulfenyl bromide, thiobenzophenone S-oxide or bis(trimethylsilyl) sulfide.

As mentioned initially, the polymercaptopolyamines according to the invention are especially suitable as hardeners for epoxy resins.

The invention relates further to a composition comprising (A) an epoxy resin having, on average, more than one 1,2-epoxy group per molecule, and (B) a compound of formula Ia or Ib.

For preparation of the compositions according to the invention, the epoxy resins customary in epoxy resin technology are suitable as component A. Examples of epoxy resins are:

I) polyglycidyl and poly(β-methylglycidyl) esters, obtainable by reacting a compound having at least two carboxyl groups in the molecule with epichlorohydrin and β-methylepichlorohydrin, respectively. The reaction is advantageously carried out in the presence of bases.

Aliphatic polycarboxylic acids may be used as the compound having at least two carboxyl groups in the molecule. Examples of such polycarboxylic acids are oxalic acid, succinic acid, glutaric acid, adipic acid, pimelic acid, suberic acid, azelaic acid and dimerised or trimerised linoleic acid.

However, cycloaliphatic polycarboxylic acids may also be used, for example tetrahydro-phthalic acid, 4-methyltetrahydrophthalic acid, hexahydrophthalic acid or 4-methylhexahydro-phthalic acid.

Aromatic polycarboxylic acids may also be used, for example phthalic acid, isophthalic acid and terephthalic acid.

II) Polyglycidyl or poly(β-methylglycidyl) ethers, obtainable by reacting a compound having at least two free alcoholic hydroxy groups and/or phenolic hydroxy groups with epichlorohydrin or β-methylepichlorohydrin under alkaline conditions, or in the presence of an acid catalyst and subsequently treating with an alkali.

The glycidyl ethers of this kind are derived, for example, from acyclic alcohols, e.g. ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylol-propane, pentaerythritol, sorbitol and also from polyepichlorohydrins. Further glycidyl ethers of this kind are derived from cycloaliphatic alcohols, e.g. 1,4-cyclohexanedimethanol, bis(4-hydroxycyclohexyl)methane or 2,2-bis(4-hydroxycyclohexyl)-propane, or from alcohols that contain aromatic groups and/or further functional groups, e.g. N,N-bis(2-hydroxyethyl)aniline or p,p'-bis(2-hydroxyethylamino)diphenylmethane. The glycidyl ethers can also be based on mononuclear phenols, such as resorcinol or hydroquinone, or on polynuclear phenols, such as bis(4-hydroxyphenyl)methane, 4,4'-dihydroxybiphenyl, bis (4-hydroxyphenyl)sulfone, 1,1,2,2-tetrakis(4-hydroxyphenyl)ethane, 2,2-bis(4-hydroxyphenyl)propane or 2,2-bis(3, 5-dibromo-4-hydroxyphenyl)propane. Further hydroxy compounds that are suitable for the preparation of glycidyl ethers are novolaks, obtainable by condensing aldehydes, e.g. formaldehyde, acetaldehyde, chloral or furfuraldehyde, with phenols or bisphenols that are unsubstituted or substituted by chlorine atoms or by $C_1$–$C_9$alkyl groups, e.g. phenol, 4-chlorophenol, 2-methylphenol or 4-tert-butylphenol.

III) Poly(N-glycidyl) compounds, obtainable by dehydrochlorination of the reaction products of epichlorohydrin with amines containing at least two amine hydrogen atoms. Such amines are, for example, aniline, n-butylamine, bis(4-aminophenyl)methane, m-xylylenediamine or bis(4-methylaminophenyl)methane.

The poly(N-glycidyl) compounds also include, however, triglycidyl isocyanurate, N,N'-diglycidyl derivatives of cycloalkylene ureas, e.g. ethylene urea or 1,3-propylene urea, and diglycidyl derivatives of hydantoins, e.g. 5,5-dimethylhydantoin.

IV) Poly(S-glycidyl) compounds, such as di-S-glycidyl derivatives derived from dithiols, e.g. ethane-1,2-dithiol or bis(4-mercaptomethylphenyl) ether.

V) Cycloaliphatic epoxy resins, e.g. bis(2,3-epoxycyclopentyl) ether, 2,3-epoxycyclo-pentylglycidyl ether, 1,2-bis (2,3-epoxycyclopentyloxy)ethane or 3,4-epoxycyclohexylmethyl 3',4'-epoxycyclohexanecarboxylate.

It is also possible, however, to use epoxy resins wherein the 1,2-epoxy groups are bound to different hetero atoms or functional groups; such compounds include, for example, the N,N,O-triglycidyl derivative of 4-aminophenol, the glycidyl ether-glycidyl ester of salicylic acid, N-glycidyl-N'-(2-glycidyloxypropyl)-5,5-dimethylhydantoin and 2-glycidyloxy-1,3-bis(5,5-dimethyl-1-glycidylhydantoin-3-yl) propane.

For preparation of the epoxy resin compositions according to the invention, preference is given to the use of a liquid or solid polyglycidyl ether or ester, especially a liquid or solid diglycidyl ether of bisphenol or a solid or liquid diglycidyl ester of a cycloaliphatic or aromatic dicarboxylic acid, or a cycloaliphatic epoxy resin. Mixtures of epoxy resins can also be used.

Suitable solid polyglycidyl ethers and esters are compounds having melting points above room temperature up to about 250° C. The melting points of the solid compounds are preferably in the range from 50 to 150° C. Such solid compounds are known and, in some cases, commercially available. It is also possible to use, as solid polyglycidyl ethers and esters, the advancement products obtained by pre-lengthening liquid polyglycidyl ethers and esters.

The epoxy resin compositions according to the invention comprise especially a liquid polyglycidyl ether or ester.

Special preference is given, as component A, to diglycidyl ethers of bisphenol A, diglycidyl ethers of bisphenol F, mixtures of a diglycidyl ether of bisphenol A and a diglycidyl ether of bisphenol F, epoxy urethanes, aliphatic epoxy resins such as trimethylolpropane triglycidyl ethers and also cycloaliphatic epoxy resins such as hexahydrophthalic acid diglycidyl ester.

The polymercaptopolyamines in accordance with the invention can advantageously be used in combination with other epoxy hardeners, especially the customary amine hardeners.

The invention accordingly relates further to a composition comprising
(A) an epoxy resin,
(B) a compound of formula Ia or Ib and
(C) a polyamine.

Examples of suitable polyamines C are aliphatic, cycloaliphatic, aromatic and heterocyclic amines, for example bis(4-aminophenyl)methane, aniline-formaldehyde resins, benzylamine, n-octylamine, propane-1,3-diamine, 2,2-dimethyl-1,3-propanediamine (neopentanediamine), hexamethylenediamine, diethylenetriamine, bis(3-aminopropyl)amine, N,N-bis(3-amino-propyl)methylamine, triethylenetetramine, tetraethylenepentamine, pentaethylenehexamine, 2,2,4-trimethylhexane-1,6-diamine, m-xylylenediamine, 1,2- and 1,4-diaminocyclohexane, bis (4-aminocyclohexyl)methane, bis(4-amino-3-methylcyclohexyl)methane, 2,2-bis(4-aminocyclohexyl)propane and 3-aminomethyl-3,5,5-trimethylcyclohexylamine (isophorone-diamine), polyaminoimidazolines and polyaminoamides, for example those derived from aliphatic polyamines and dimerised or trimerised fatty acids. Also suitable as amines (C) are the polyoxyalkyleneamines from Texaco known as Jeffamines'; for example Jeffamine' EDR148, D230, D400 and T403.

Further suitable polyamines (C) are 1,14-diamino-4,11-dioxatetradecane, dipropylene-triamine, 2-methyl-1,5-pentanediamine, N,N'-dicyclohexyl-1,6-hexanediamine, N,N'-dimethyl-1,3-diaminopropane, N,N'-diethyl-1,3-diaminopropane, N,N-dimethyl-1,3-diaminopropane, secondary polyoxypropylene-di- and -triamines, 2,5-diamino-2,5-dimethylhexane, bis(amino-methyl)tricyclopentadiene, m-aminobenzylamine, 1,8-diamino-p-menthane, bis(4-amino-3,5-dimethylcyclohexyl)methane, 1,3-bis(aminomethyl)cyclohexane, dipentylamine, bis(4-amino-3,5-diethylphenyl)methane, 3,5-diethyltoluene-2,4-diamine and 3,5-diethyltoluene-2,6-diamine.

As component C of the substance mixtures in accordance with the invention, preference is given to cycloaliphatic and aliphatic amines, especially the amines of formulae $R_5$—NH—$R_2$ and E—NHR$_2)_{m+l}$ used for preparation of the polymercaptopolyamines according to the invention.

The ratio of amounts of components A and B and, where applicable, C in the compositions according to the invention can vary within wide limits. The optimum ratio is dependent upon, inter alia, the kind of amine, and can be readily determined by the person skilled in the art.

Component B and, where applicable, component C are preferably used in amounts such that the sum of the amine and mercaptan equivalents is from 0.5 to 2.0 equivalents, especially from 0.8 to 1.5 equivalents, and more especially from 0.9 to 1.2 equivalents, based on one epoxy equivalent.

The compositions according to the invention may optionally comprise accelerators, for example tertiary amines or imidazoles.

Furthermore, the curable mixtures may comprise tougheners, for example core/shell polymers or the elastomers or elastomer-containing graft polymers known to the person skilled in the art as rubber tougheners.

Suitable tougheners are described, for example, in EP-A-449 776.

In addition, the curable mixtures may comprise fillers, for example metal powder, wood flour, glass powder, glass beads, semi-metal and metal oxides, e.g. $SiO_2$ (Aerosils, quartz, quartz powder, fused silica powder), corundum and titanium oxide, semi-metal and metal nitrides, e.g. silicon nitride, boron nitride and aluminium nitride, semi-metal and metal carbides (SiC), metal carbonates (dolomite, chalk, $CaCO_3$), metal sulfates (barytes, gypsum), ground minerals and natural or synthetic minerals chiefly of the silicate series, e.g. zeolites (especially molecular sieves), talcum, mica, kaolin, wollastonite, bentonite and others.

In addition to the additives mentioned above, the curable mixtures may also comprise further customary additives, e.g. antioxidants, light stabilisers, plasticisers, dyes, pigments, thixotropic agents, toughness improvers, antifoams, antistatics, lubricants and mould-release agents.

The curing of the epoxy resin compositions according to the invention to form mouldings, coatings or the like is carried out in a manner customary in epoxy resin technology, for example as described in "Handbook of Epoxy Resins", 1967, by H. Lee and K. Neville.

Special mention should be made of the high reactivity of the polymercaptopolyamines according to the invention with respect to epoxy resins even at low temperatures (from −5° C. to 25° C.).

The curable mixtures exhibit only a slight tendency to carbonatisation (becoming cloudy). The cured products are distinguished by surprisingly high resistance to chemicals and resistance to weathering.

The invention relates further to the cross-linked products obtainable by curing a composition according to the invention.

The compositions according to the invention are excellently suitable as a coating composition, adhesive, bonding composition for composite materials or casting resin for the manufacture of mouldings.

EXAMPLES

I. Preparation of Compounds of Formula Ia and Ib a) General procedure for the preparation of polyepisulfides:

The epoxy compounds of formula IIa or IIb are dissolved in an amount of solvent that is from 0.5 to 5 times the amount of the epoxy compound and is stirred, under nitrogen, with thiourea or alkali-metal or ammonium thiocyanate (0.8–1.2 equivalents of sulfur per epoxy equivalent) at 60–100° C. until the epoxy content has fallen to nearly zero.

After separating off the by-products by means of filtration, extraction or phase separation, the polyepisulfide is isolated as a result of concentration by evaporating off the solvent.

b) General Procedure for the Preparation of Polymercaptopolyamines:

The polyepisulfide is dissolved in an amount of solvent that is from 0.5 to 5 times the amount of the polyepisulfide and under nitrogen and with vigorous stirring, is combined with the amine (either $R_5$—NH—$R_2$ or E—$(NHR_2)_{m+1}$), which likewise has been dissolved in an amount of solvent that is from 0.5 to 5 times the amount of the amine. The amount of amine is selected so that there are from 1 to 10 amine groups for one episulfide group. After stirring at 60–100° C. for from 0.2 to 3 hours, the solvent is distilled off under reduced pressure. To isolate the polymercaptopolyamine of formula Ia or Ib, the excess amine reagent is removed by means of vacuum distillation at elevated temperature. In one embodiment of the invention, the excess amine is not removed and the mixture of the excess amine and the polymercaptopolyamine of formula Ia or Ib is used as a hardener for epoxy resins.

In accordance with the above-mentioned procedure, polymercaptopolyamines according to the invention (Examples I.1–I.46) are prepared from the following amines and epoxy compounds of formula IIa or IIb:

BA: n-butylamine
GA: n-octylamine
CYA: cyclohexylamine
BZA: benzylamine
MBA: methylbutylamine
DMDP: N,H-demethyl-1,3-diaminopropane
MDP: N-methyl-1,3-diaminopropane
DACY: 1,2-diaminocyclohexane
AEP: N-2-aminoethylpiperazine
DETA: diethylenetriamine
IPD: isophoronediamine
MXDA: meta-xylylenediamine
DYTEK-A: 1,5-diamino-2-methylpentane
NBDA: isomeric mixture of 2,5- and 2,6-bis(aminomethyl)norbornane
EDA: ethylenediamine
epoxide 1: liquid diglycidyl ether of bisphenol A having an epoxy content of 5.25–5.4 eq./kg
epoxide 2: liquid mixture of diglycidyl ether of bisphenol A and diglycidyl ether of bisphenol F having an epoxy content of 5.5–5.8 eq./kg
epoxide 3: 1,4-bis(hydroxymethyl)cyclohexane diglycidyl ether
epoxide 4: epoxy phenol novolak having an epoxy content of 5.6–5.8 eq/kg
epoxide 5: diglycidyl ether of hydrogenated bisphenol A
epoxide 6: tetraglycidyl ether of formula

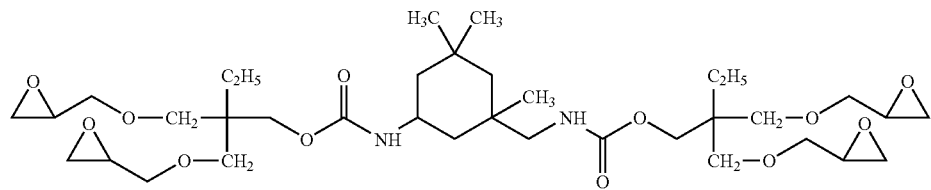

epoxide 7: di(β-methylglycidyl) ether of bisphenol A
epoxide 8: trimethylolpropane triglycidyl ether
epoxide 9: hexahydrophthalic acid diglycidyl ester (epoxy content: 5.6–6.2 eq./kg)
epoxide 10: phenyl glycidyl ether The reaction conditions and the properties of the final products are listed in Table 1.

TABLE 1

| Example | Starting products amine | epoxide | molar ratio episulfide/amine | T/° C. | viscosity [mPa · s] | amine value [equivalents/kg] |
|---|---|---|---|---|---|---|
| I.1 | DETA | epoxide 1 | 1:5 | 100 | 1900*⁾ | 10.5 |
| I.2 | DETA | epoxide 1 | 1:5 | 100 | >50 000 | 7.1 |
| I.3 | IPD | epoxide 1 | 1:5 | 100 | 5300*⁾ | 7.6 |
| I.4 | MXDA | epoxide 1 | 1:5 | 60 | 2030*⁾ | 9.6 |
| I.5 | MXDA | epoxide 1 | 1:5 | 60 | >50 000 | — |
| I.6 | MXDA | epoxide 1 | 1:4 | 60 | 9000*⁾ | 8.5 |
| I.7 | MXDA | epoxide 2 | 1:5 | 55 | 2200*⁾ | 9.2 |
| I.8 | MXDA | epoxide 2 | 1:4 | 55 | 4400*⁾ | 8.1 |
| I.9 | MXDA | epoxide 2 | 1:3 | 55 | 50 000*⁾ | 7.6 |
| I.10 | IPD | epoxide 2 | 1:5 | 100 | 27 000*⁾ | 7.8 |
| I.11 | IPD | epoxide 2 | 1:3 | 100 | >50 000 | 6.3 |
| I.12 | DETA | epoxide 2 | 1:5 | 100 | 2000*⁾ | — |
| I.13 | DYTEK-A | epoxide 2 | 1:5 | 100 | 1600*⁾ | 10.0 |
| I.14 | NBDA | epoxide 2 | 1:5 | 60 | 13 500*⁾ | 8.4 |
| I.15 | EDA | epoxide 2 | 1:5 | 100 | >50 000 | — |
| I.16 | MXDA | epoxide 3 | 1:5 | 60 | 300*⁾ | 9.8 |
| I.17 | MXDA | epoxide 3 | 1:4 | 60 | 500*⁾ | 8.8 |
| I.18 | IPD | epoxide 3 | 1:4 | 60 | 970*⁾ | — |
| I.19 | DETA | epoxide 3 | 1:5 | 100 | >50 000 | — |
| I.20 | BA | epoxide 2 | 1:10 | 77 | >60 000 | 2.6 |
| I.21 | CYA | epoxide 2 | 1:10 | 100 | >60 000 | 3.3 |
| I.22 | BZA | epoxide 2 | 1:10 | 100 | >60 000 | 2.8 |
| I.23 | OA | epoxide 2 | 1:10 | 90 | >60 000 | — |
| I.24 | CYA | epoxide 4 | 1:10 | 100 | >60 000 | 4.1 |
| I.25 | BZA | epoxide 4 | 1:10 | 100 | >60 000 | 3.6 |
| I.26 | BA | epoxide 3 | 1:10 | 80 | 3000–7000 | 2.9 |
| I.27 | CYA | epoxide 3 | 1:10 | 100 | >60 000 | 3.1 |
| I.28 | BZA | epoxide 3 | 1:10 | 100 | 10 200 | 3.0 |
| I.29 | OA | epoxide 3 | 1:10 | 100 | | |
| I.30 | BA | epoxide 5 | 1:10 | 75 | >128 000 | 2.15 |
| I.31 | MBA | epoxide 5 | 1:10 | 75 | 13 440 | — |
| I.32 | BA | epoxide 6 | 1:20 | 75 | >128 000**⁾ | 2.04 |
| I.33 | MBA | epoxide 6 | 1:20 | 60 | 12 800 | — |
| I.34 | IPD | epoxide 6 | 1:20 | 60 | >128 000**⁾ | 7.83 |
| I.35 | DMDP | epoxide 3 | 1:10 | 70 | 1400 | 7.42 |
| I.36 | MDP | epoxide 3 | 1:10 | 65 | 43 520 | 6.17 |
| I.37 | DACY | epoxide 3 | 1:5 | 65 | 840 | 10.71 |
| I.38 | AEP | epoxide 3 | 1:5 | 65 | 400 | 10.45 |
| I.39 | MBA | epoxide 3 | 1:2 | 67 | 1040 | — |
| I.40 | BA | epoxide 7 | 1:10 | 70 | >128 000 | 3.10 |
| I.41 | DACY | epoxide 3 | 1:2 | 75 | 87 040 | 6.34 |
| I.42 | AEP | epoxide 3 | 1:2 | 77 | 11 520 | 6.72 |
| I.43 | MBA | epoxide 6 | 1:15 | 80 | 1160 | — |
| I.44 | MBA | epoxide 8 | 1:3 | 70 | >128 000 | — |

TABLE 1-continued

| Example | Starting products amine | epoxide | molar ratio episulfide/ amine | T/° C. | viscosity [mPa · s] | amine value [equivalents/kg] |
|---|---|---|---|---|---|---|
| I.45 | IPD | epoxide 10 | 2:1 | 75 | >128 000 | 2.83 |
| I.46 | BA | epoxide 10 | 1:5 | 78 | 3040 | 2.75 |

*)mixture of amine and polymercaptopolyamine; excess amine not distilled off
**)practically a gel Application Examples II.1 Polymercaptopolyamine as Hardener for Epoxy Resins 100 g of a liquid diglycidyl ether of bisphenol A having an epoxy content of 5.25–5.4 eq./kg are mixed with 28 g of the polymercaptopolyamine of Example I.4 at 20° C. The mixture is applied to glass plates or steel plates using a doctor blade (thickness of layer: 0.2 mm) and fully cured for 10 days at 20° C.

For comparison purposes, 100 g of the same epoxy resin are fully cured using 20 g of a commercially available amine hardener (DETA) under the same conditions.

The fully cured coatings exhibit the properties listed in Table 2.

TABLE 2

| Example II.1 | according to the invention (polymercaptopolyamine) | comparison (DETA) |
|---|---|---|
| viscosity (DIN 53018 T1/76) [mPa · s] | 5600 | 8650 |
| gel time according to TECAM at 20° C.[min] | 35 | 15 |
| dust-dry time [h] | | |
| at 20° C. | 2.0 | >30 |
| at 5° C. | 2.5 | >30 |
| exudation at 5° C. | none | considerable |
| hardness according to Persoz (ISO 1552) [s] at 20° C. | | |
| after 1 day | 358 | 340 |
| after 1 week | 383 | 365 |
| after 1 month | 394 | 355 |
| hardness according to Persoz (ISO 1552) [s] at 5° C. | | |
| after 1 day | 235 | 80 |
| after 1 week | 267 | 220 |
| after 1 month | 386 | 250 |

II.2 Polymercaptopolyamine as Co-hardener in Admixture with Other Polyamine Hardeners 100 g of a liquid diglycidyl ether of bisphenol A having an epoxy content of 5.25–5.4 eq./kg are mixed with 17 g of a commercially available amine hardener (DETA) and 4.2 g of the polymercaptopolyamine of Example I.5. The mixture is processed and fully cured as described in Example II.1.

For comparison purposes, the above-mentioned mixture without the addition of the polymercaptopolyamine is fully cured under the same conditions.

The fully cured coatings exhibit the properties listed in Table 3.

TABLE 3

| Example II.2 | according to the invention (polymercaptopolyamine + DETA) | comparison (DETA) |
|---|---|---|
| gel time according to TECAM at 20° C. [min] | 19 | 15 |
| dust-dry time [h] at 20° C./ 65% rel. humidity | 4 | >30 |
| full hardening time [h] at 20° C./65% rel. humidity | 13 | >30 |
| hardness according to Persoz (ISO 1552) [s] | | |
| after 1 d at 20° C. | 310 | 195 |
| after 7 d at 20° C. | 349 | 229 |
| after 1 d at 5° C. | 73 (tacky) | 24 (tacky) |
| after 7 d at 5° C. | 148 (tacky) | 39 (tacky) |

II.3 Polymercaptopolyamine as Hardener for Epoxy Resins

The polymercaptopolyamine prepared according to Example I.26 is mixed with the epoxy resins and further additives listed in Table 4 and fully cured.

The properties of the mixtures and of the cured products are likewise listed in Table 4.

TABLE 4

| | Example | | |
|---|---|---|---|
| | II.3.1 | II.3.2 | II.3.3 |
| epoxide 9 [g] | 41 | | |
| epoxide 8 [g] | | 37.4 | |
| epoxide 6 [g] | | | 43.32 |
| polymercaptopolyamine [g] | 29 | 32.6 | 26.68 |
| TiO$_2$ (Kronos 2310) [g] | 30 | 30 | 30 |
| flow improver BYK 300 [g] | 0.14 | 0.14 | 0.14 |
| methyl ethyl ketone [g] | | | 8.8 |
| viscosity (Epprecht viscosimeter) at 20° C. | | | |
| of freshly prepared mixture [mPa · s] | 5760 | 3520 | 2720 |
| after 60 min [mPa · s] | >128 000 | >128 000 | 76 800 |
| curing for 12 days at RT | | | |
| hardness according to Persoz [s] | 20 | 24 | 63 |
| impact deformation[1] (direct impact) [cm · kg] | >160 | 30 | >60 |
| impact deformation (reverse impact) [cm · kg] | >80 | 20 | >20 |
| Erichsen indentation test[2] [mm] | 10.5 | 8.9 | 9.3 |
| acetone test | 2 | 2 | 1–2 |

TABLE 4-continued

|  | Example | | |
|---|---|---|---|
|  | II.3.1 | II.3.2 | II.3.3 |
| curing for 30 min at 80° C. and 12 d at RT | | | |
| hardness according to Persoz [s] | 20 | 26 | 113 |
| impact deformation[1]) (direct impact) [cm · kg] | >160 | >30 | >60 |
| impact deformation (reverse impact) [cm · kg] | >80 | >10 | >30 |
| Erichsen indentation test[2]) [mm] | 10.6 | 9.1 | 9.8 |
| acetone test[3]) | 2 | 2 | 1 |

[1])The impact deformation (direct impact) is determined by dropping a punch having a weight of 2 kg, on the underside of which there is a sphere 20 mm in diameter, directly onto the coated surface from a certain height, underside down. The value given is the product of the weight of the punch in kg and the maximum test height in cm at which no damage to the coating can be found. In impact deformation (reverse impact) the punch is dropped onto the face remote from the coating.
[2])according to DIN 53156
[3])according to DIN 53320. The specimen is held in acetone for 1 min. The result is assessed according to the following five-point scale: 0 = unchanged; 1 = not scratchable with a finger nail but drags; 2 = difficult to scratch; cotton wool may be stained; 3 = softened, readily scratched; 4 = starting to come away or dissolve away; 5 = dissolved away completely.

What is claimed is:

1. A composition comprising:
   (A) an epoxy resin and
   (B) a compound of formula Ia or Ib

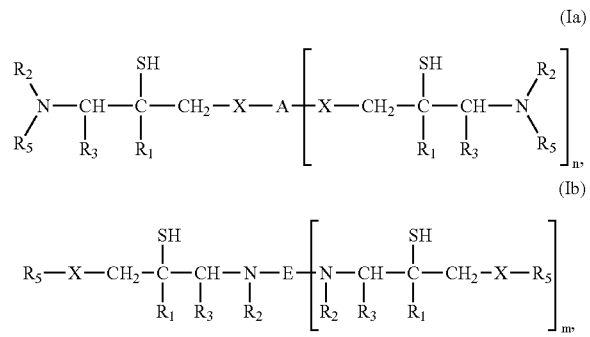

wherein A is an (n +1)-valent aliphatic, cycloaliphatic, araliphatic or aromatic radical and n is an integer from 0 to 5, E is an (m +1)-valent aliphatic, cycloaliphatic, araliphatic or aromatic radical and m is an integer from 0 to 3, X in formula Ia is —O—, C(═O)O, or when $R_3$ is not hydrogen, —CHR$_4$— with $R_4$ and $R_3$ together forms an ethylene group, X in formula Ib is —O—, C(═O)O, $R_1$ and $R_2$ are, each independently of the other, hydrogen or methyl, $R_3$ is hydrogen, or in formula Ia, $R_3$ and $R_4$ together form an ethylene group, and $R_5$ is a monovalent aliphatic, cycloaliphatic, araliphatic or aromatic radical.

2. The composition according to claim 1 further comprising (C) a polyamine.

3. The composition according to claim 1 comprising component B in such amounts that the sum of the amine and mercaptan equivalents is from 0.5 to 2.0 equivalents, based on one epoxy equivalent.

4. A cross-linked product obtained by curing a composition according to claim 1.

5. The composition according to claim 1, wherein in the compound of formula Ia, X is —O— and A is a bivalent radical of a bisphenol or of a cycloaliphatic diol, a radical of a phenol novolak or cresol novolak, a bi- to tetra-valent radical of an isocyanate/polyol adduct or a tri- to hexa-valent radical of a tri- to hexa-functional aliphatic polyol.

6. The composition according to claim 1, wherein in the compound of formula Ia, X is —O— and A is a bivalent radical of formula

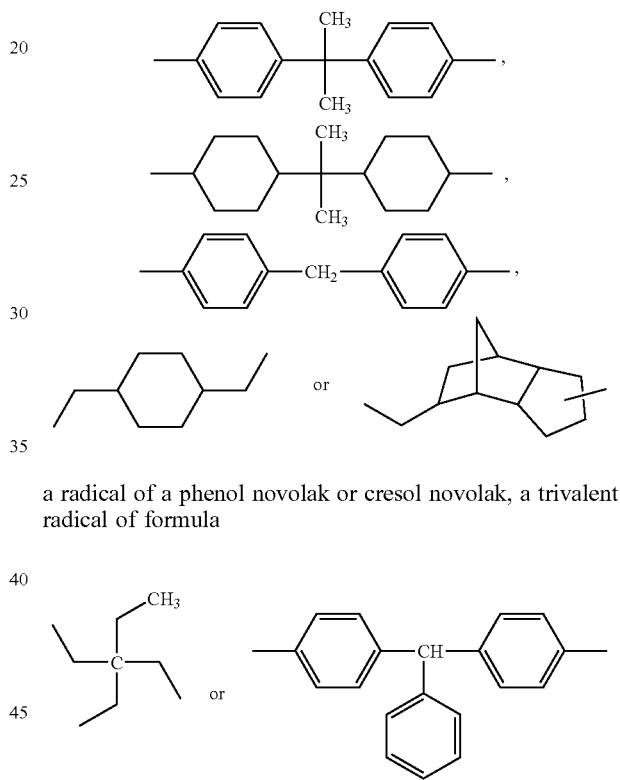

a radical of a phenol novolak or cresol novolak, a trivalent radical of formula or a tetravalent radical of formula

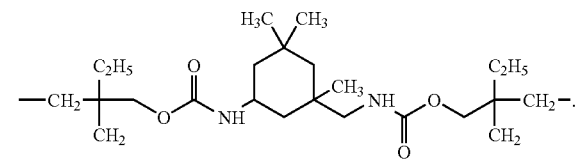

7. The composition according to claim 1, wherein $R_5$ is $C_1$–$C_{20}$alkyl, $C_5$–$C_{12}$- cycloalkyl, $C_6$–$C_{10}$aryl or $C_7$–$C_{12}$aralkyl, each of which is unsubstituted or substituted by one or more amino groups, hydroxyl groups, $C_1$–$C_8$alkoxy groups or halogen atoms.

8. The composition according to claim 1, wherein $R_5$ is $C_2$–$C_{10}$alkyl $C_2$–$C_{10}$aminoalkyl, phenyl, benzyl, cyclohexyl or a radical of formula $H_2N$—Z—$CH_2$—NH—, wherein Z is a bivalent cycloaliphatic, araliphatic or aromatic radical of formula —$(CH_2CH_2NH)_k$—$CH_2$—, wherein k is 2 or 3.

9. The composition according to claim 1, wherein $R_5$ is n-butyl, n-octyl, cyclohexyl, benzyl, 2-aminoethyl, 4-(aminomethyl)pentyl, 5-amino-2-methylpentyl, 3-dimethylaminopropyl, 3-methylaminopropyl, 4-aminocyclohexyl or a radical of formula

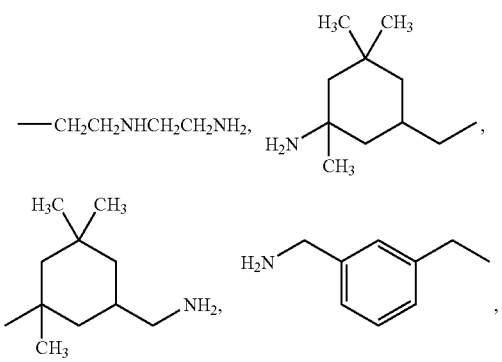

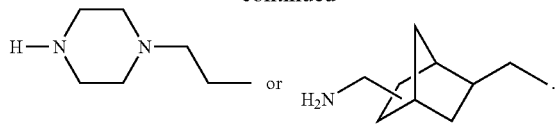

10. The composition according to claim 1, wherein X is O— and $R_1$ and $R_3$ are hydrogen.

11. The composition according to claim 2, wherein the polyamine is a cycloaliphatic or aliphatic amine.

12. The composition according to claim 11, wherein the polyamine has the formula $R_5$—NH—$R_2$ or E—$(NHR_2)_{m+1}$, wherein $R_5$, $R_2$, E and m are defined as in claim 1.

13. The composition according to claim 3 comprising component B in such amounts that the sum of amine and mercaptan equivalents is from 0.8 to 1.5 equivalents, based on one epoxy equivalent.

14. The composition according to claim 13 comprising component B in such amounts that the sum of amine and mercaptan equivalents is from 0.9 to 1.2 equivalents, based on one epoxy equivalent.

15. The composition according to claim 1, wherein X is —O— or —C(=O)O.

* * * * *